United States Patent [19]

Kathawala

[11] 4,008,327

[45] Feb. 15, 1977

[54] TOLYLOXYPIVALOPHENONE DERIVATIVES

[75] Inventor: Faizulla G. Kathawala, West Orange, N.J.

[73] Assignee: Sandoz, Inc., E. Hanover, N.J.

[22] Filed: June 16, 1975

[21] Appl. No.: 587,345

[52] U.S. Cl. .......................... 424/278; 260/340.6; 260/340.9; 260/592
[51] Int. Cl.$^2$ ..................................... A61K 31/335
[58] Field of Search ................ 260/340.9; 424/278

[56] References Cited

UNITED STATES PATENTS 3,426,036 2/1969 Biel et al. .......................... 260/297

*Primary Examiner*—Ethel G. Love
*Attorney, Agent, or Firm*—Gerald D. Sharkin; Richard E. Vila; Frederick H. Weinfeldt

[57] ABSTRACT

The compounds are cyclic acetals of 4'-($\alpha$-hydroxy-$\alpha$-alkyl-p-tolyloxy)pivalophenones, e.g., ethylene glycol acetal of 4'-($\alpha$-hydroxy-$\alpha$-heptadecyl-p-tolyloxy)-pivalophenone, and are useful as anti-diabetic agents.

16 Claims, No Drawings

TOLYLOXYPIVALOPHENONE DERIVATIVES

This invention relates to organic compounds, and more particularly to derivatives of p-tolyloxypivalophenone and to pharmaceutical compositions containing such compounds, as well as to the use of such compounds as pharmaceuticals.

The compounds of this invention are conveniently represented by the formula I:

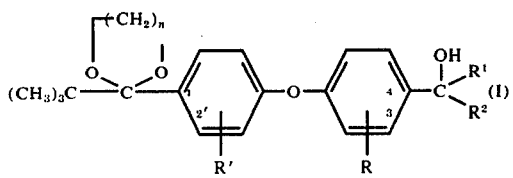

wherein each of
R and R' is independently, a hydrogen atom, alkyl having from 1 to 4 carbons, or fluoro or chloro, i.e., a halogen atom having an atomic weight of from about 19 to 36;
$R^1$ is alkyl having from 1 to 24 carbon atoms;
$R^2$ is a hydrogen atom, alkyl having from 1 to 4 carbon atoms; and
$n$ is 1 or 2;
provided that when R is at the 3-position, or R' is at the 2'-position, it is not branched chain alkyl, i.e., that the ring carbon atoms adjacent (ortho) to the 1'- or 4-positions should not bear a branched chain alkyl substituent.

In the above-presented definitions of alkyl groups suitable as R, R', $R^1$ and $R^2$, it is to be understood that when any of them have from 1 to 4 carbon atoms, the alkyl portion thereof may be methyl, ethyl, n-propyl or isopropyl, as well as the unbranched or branched forms of butyl. In addition, when $R^1$ is alkyl, having from 5 to 24 carbon atoms (i.e., a higher alkyl moiety) it may be, e.g., pentyl, hexyl, octyl, decyl, dodecyl, tetradecyl, hexadecyl or octadecyl, which may be branched or unbranched.

Compounds I may be obtained by process a), i.e., by condensing a Grignard agent of formula II

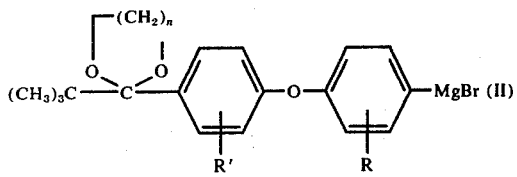

wherein $n$, R and R' are as defined above, with a carbonyl compound of formula III:

wherein $R^1$ and $R^2$ are as defined above; in the presence of an aprotic solvent and under essentially anhydrous conditions, to obtain a corresponding Grignard adduct, which is then hydrolyzed to the corresponding compound I.

The preparation of a Compound I (process a) is conveniently carried out in the manner, and under the conditions conventionally applied in carrying out the well-known Grignard reactions. Convenient temperatures are those of from about 0° to 70° C, preferably at the reflux temperature of the solvent. Suitable aprotic solvents are ethers, such as tetrahydrofuran and diethyl ether.

The hydrolysis of the resulting adduct to yield a compound I may be carried out in the manner conventionally employed in hydrolyzing Grignard adducts, e.g., by treating the Grignard adduct with water, or an aqueous salt, acid or base, e.g., saturated ammonium chloride solution.

Compounds II, used in process a), may be obtained in the conventional manner for the preparation of a Grignard reagent (process b); for example, by reacting a compound of the formula IV:

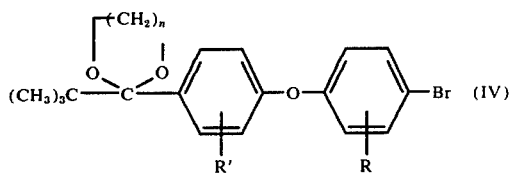

wherein $n$, R and R' are as defined above, with magnesium metal at temperatures and in a solvent suitable for carrying out process (a), under essentially anhydrous conditions. A small amount of solid iodine may be added to aid in initiating the reaction, as is commonly done in preparing Grignard reagents. Avoidance of moisture to achieve essentially anhydrous conditions as is conventionally practiced in preparing Grignard reagents is exercised, e.g., by employing, "dry" solvents and moisture-free apparatus. It is particularly convenient to prepare Compounds II, in situ, and react directly with Compound III, without recovery.

Compounds IV, used in process (b), are obtainable by ketalization (process c) of corresponding Compounds V:

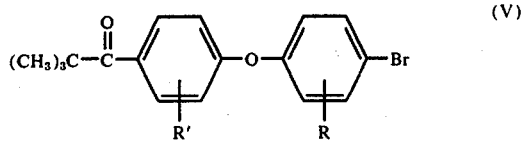

wherein R and R' are as defined above.

Process (c) is conveniently conducted by reacting a Compound V with a glycol of the formula G:

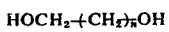

wherein $n$ is as defined above, in the presence of an aromatic sulfonic acid and an inert aromatic solvent at elevated temperatures, e.g., in the range of from about 80° to 140° C., preferably at the reflux temperature of the system, e.g., for a period of time between 12 and 60 hours. Although the particular aromatic sulfonic acid employed is not critical, p-toluene sulfonic acid is preferred. Suitable inert aromatic solvents include benzene, xylene and toluene; the latter being particularly preferred.

Compounds V, used in process (c) are obtainable by brominating (process d) a corresponding p-phenoxypivalophenone of formula VI:

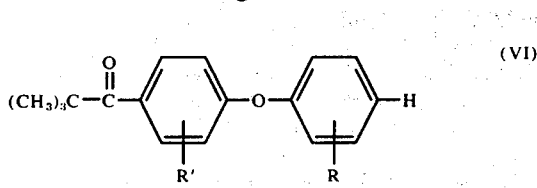

wherein R and R' are as defined above.

The bromination (process d) may be carried out by treating a compound VI with molecular bromine in an inert solvent, such as carbon tetrachloride (CCl$_4$), at moderate temperatures, e.g., from about 0° to 35° C in the presence of a small amount of a Friedel-Crafts reagent, e.g., FeCl$_3$ as a catalyst.

The compounds of formula VI may be prepared by reacting under Grignard Reaction Conditions, (process e) a compound of the formula VII:

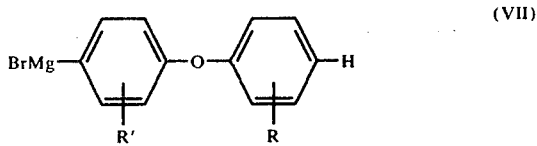

in which R and R' are as defined, with trimethylacetyl-chloride, i.e., the compound of the formula VIII:

and hydrolyzing the resulting adduct.

Process (e) may conveniently be carried out at temperatures in the range of from about 0° to 100° C, and in the presence of an inert, organic solvent, such as the cyclic and acyclic ethers, such as diethyl ether and tetrahydrofuran. Hydrolysis of the resulting adduct may be carried out in the same manner as described above in connection with process (a). Compounds VII are Grignard reagents and may be prepared from the corresponding p-bromo compounds in the same general manner as described above in connection with process (b).

It will be noted that the Grignard reagents involved in the above-described series of reactions are indicated as magnesium bromides. However, if desired, magnesium iodides may be similarly employed, hence, iodine occurring at each instance where bromine is indicated; bromine, however, is preferred.

The products of the above-described reactions may be recovered and refined in conventional manner, e.g., by crystallization, distillation or chromatographic techniques, such as eluting from a chromotographic column or separating on a silica layer.

Starting materials and reagents used in the above-described reactions, e.g., Compounds III, VI, VII, VIII, and G are either known and obtained by methods described in the literature, or where not known, may be obtained by methods analogous to those described in the literature. Some of the reactants and starting materials are commercially available.

The above-described series of reactions (processes a through e) are conveniently represented in the following Reaction Scheme wherein n, R, R', R$^1$ and R$^2$ are as defined above.

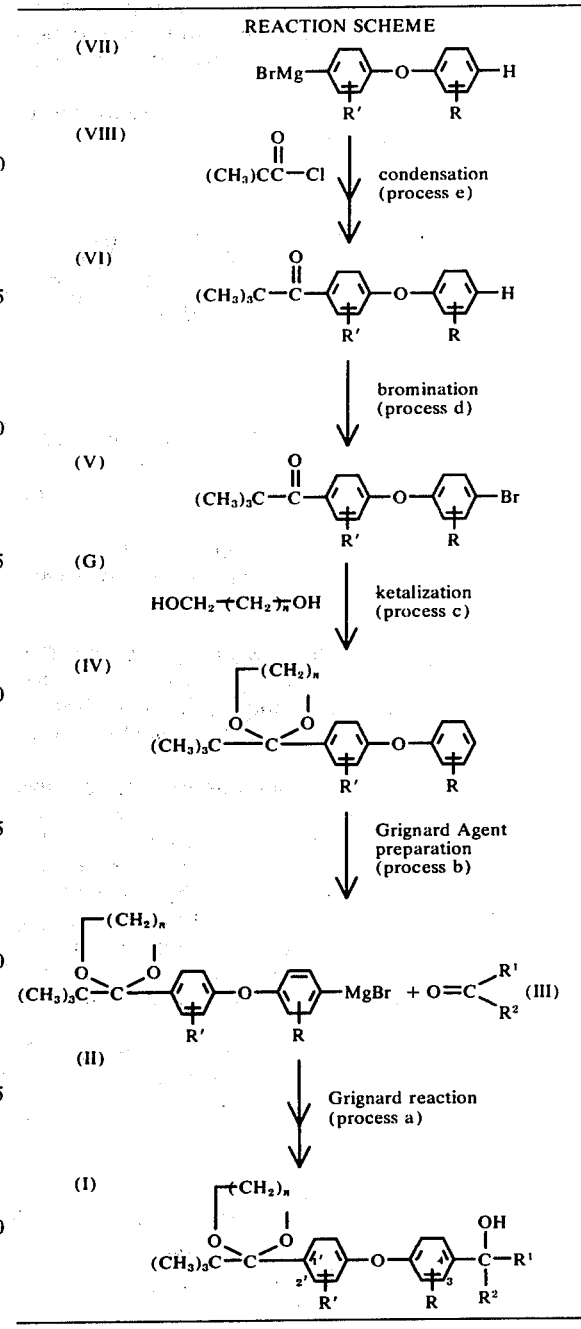

STATEMENT OF UTILITY

The compounds of formula I are useful because they possess pharmacological activity, particularly as antidiabetic agents, i.e., in the treatment of diabetes whether the onset was during the juvenile or mature period, in mammals as indicated by the lowering of blood glucose in loading and non-loading hypoglycemic tests. In the glucose-loading test 6 to 8-week old male Royal Hart mice weighing 30 to 35 grams are fasted in groups of 5 for 16 hours and then are given from 10 to 200 milligrams per kilogram of animal body weight of the test compound orally. One and one-half hours later, the mice are given orally 2 grams per kilogram of animal body weight of a glucose challenge. Twenty-five minutes later, the mice are anesthetized with 85 milligrams per kilogram of animal body weight of sodium hexobarbital and 5 minutes later blood is collected via cardiac puncture. The blood samples are placed in an autoanalyzer cup containing 0.025 milliliters of heparin (1,000 units per milliliter); and the samples are capped, shaken, and stored in ice. The glucose content is determined by the autoanalyzer potassium ferric-cyanide N-2b method and are compared with a control group, which receives orally 0.5% carboxymethyl cellulose vehicle and are run concurrently. The non-loading test is carried out in the same manner, except that anesthetizing and blood collecting are done two hours after administrating the test compound and the glucose loading is omitted.

For such usage, the compounds (I) may be combined with a pharmaceutically-acceptable carrier or adjuvant and may be administered orally or parenterally as such or admixed with conventional pharmaceutical carriers. They may be administered in such forms as tablets, dispersible powders, granules, capsules, syrups and elixirs, and parenterally as solutions, suspensions, dispersions, emulsions and the like, e.g., a sterile injectable aqueous formulation. These pharmaceutical compositions may contain from about 0.5% up to about 90% of the active ingredient in combination with the carrier or adjuvant, more usually between 10% and 70% by weight. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation.

The anti-diabetic effective dosage of compounds (I) employed in the treatment of diabetes will vary depending on the particular compound employed and the severity of the condition being treated. However, in general, satisfactory results are obtained when the compounds of formula (I) are administered at a daily dosage of from about 10 to about 200 milligrams per kilogram of animal body weight, perferably given in divided doses two to four times per day, or in sustained release form. For most large mammals, the total daily dosage is from about 750 milligrams to about 3,000 milligrams. Dosage forms suitable for internal use comprise from about 190 to about 1500 milligrams of active compound in intimate admixture with a solid or liquid pharmaceutically-acceptable carrier or diluent. In general, oral administration is preferred, particularly tablets and solid or liquid diluent-filled capsules, as appropriate to the nature of the particular active ingredient.

A representative formulation suitable for oral administration 2 to 4 times a day for the treatment of diabetes are liquid-filled soft gelatin capsules prepared by standard encapsulating techniques which contain the following:

| Ingredient | Weight (mg) |
|---|---|
| 4'-(α-hydroxy-α-heptadecyl-p-tolyloxy)-pivalophenone, ethylene glycol acetal | 200 |
| inert liquid diluent (peanut or sesame oil) | 100 |

The compounds I in which $R^2$ has from 12 to 20 carbon atoms are generally preferred. Compounds I wherein each of R, R' and $R^2$ is a hydrogen atom, e.g., the product of Example 1, are also generally perferred.

In the following examples, which are illustrative of the invention, temperatures are in degrees centigrade, and room temperature is 20° to 30° C., unless indicated otherwise.

EXAMPLE 1

4'-(α-hydroxy-α-heptadecyl-p-tolyloxy)-pivalophenone, ethylene glycol acetal.

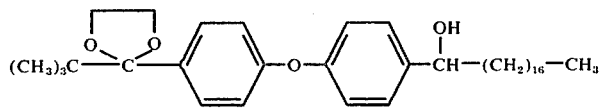

Step A. Preparation of p-phenoxy-pivalophenone (a compound VI)

To a flask containing 33.6 g. of magnesium and a few crystals of iodine, is added 50 to 70 ml. of a solution of 300 g. of 4-bromodiphenyl ether in 500 ml. of absolute tetrahydrofuran. The remainder of the solution is added as needed to maintain a gentle reflux and the resulting mixture heated to reflux for 30 minutes. The resulting mixture is then added to a solution of trimethylacetyl chloride in 500 ml. of absolute tetrahydrofuran at a rate so as to maintain a temperature of from 40° to 50° C. The resulting mixture is then stirred at ambient temperature for 1 hour. 200 ml. of 2N. hydrochloric acid is then added. The organic layer is washed twice with one liter of 2N. sodium carbonate solution, dried and evaporated in vacuo to a liquid. The liquid thus obtained is distilled under reduced pressure to obtain p-phenoxypivalophenone, b.p. 136°–139° C. at 0.1 mm/Hg.

Step B: Preparation of p-bromophenoxypivalophenone (a compound V)

To a solution of 100 g. of p-phenoxypivalophenone in 2 l. of carbontetrachloride is added 5 g. ferric chloride and then dropwise a solution of 64 g. bromine in 100 ml. carbon tetrachloride over a period of 1 hour. The mixture is stirred at room temperature for 3 days; thereafter the organic phase is washed three times with saturated aqueous sodium sulfite solution, washed with water, dried over sodium sulfate (anhydrous), filtered and evaporated in vacuo to dryness to yield a clear oil. The clear oil is crystallized from pentane to give p-bromophenoxypivalophenone, m.p. 73°–74° C.

Step C: Preparation of 2-(t.-butyl)-2-4-(4'-bromophenoxyphenyl)-1,3-dioxolane (a compound IV)

A mixture of 100 g. of p-bromophenoxypivalophenone, 100 ml. ethylene glycol and 1.5 g. p-toluenesulfonic acid in 1500 ml. toluene is refluxed with a Dean-Stark trap for 48 hours to remove water formed in the reaction. The resultant toluene solution is extracted several times with 10% sodium bicarbonate solution, washed with water, dried over potassium carbonate (anhydrous), filtered and evaporated in vacuo to dryness to give a residue. From the residue is crystallized with pentane, the title bromo-product, m.p. 84°–86° C.

Step D:Preparation of 4'-(α-hydroxy-α-heptadecyl-p-tolyloxy)-pivalophenone, ethylene glycol acetal To a flask containing 1.5 g. magnesium and a few crystals of iodine is added a solution of 17.7 g 2-(t-butyl)-2-4-(4'-bromo-phenoxyphenyl)-1,3-dioxolane in 60 ml. absolute tetrahydrofuran. The resulting solution is refluxed for 1 hour to insure complete reaction. The cooled solution is diluted to 150 ml. with tetrahydrofuran and a solution of 13.0 g. n-octadecanal in 200 ml. absolute tetrahydrofuran is added dropwise. After stirring the reaction mixture at room temperature for 16 hours, 300 ml. of saturated ammonium chloride is added, then 500 ml. ether; the organic layer separated, washed well with water, dried over anhydrous sodium sulfate, filtered and evaporated under vacuum to dryness. The residue is chromatographed on a silica gel column eluting with benzene, and the fraction containing the desired material collected. On evaporation of the solvent, the desired title compound is obtained as an oil.

Repeating the procedure of this example, but replacing the ethylene glycol used in Step C, with an approximately equivalent amount of propylene glycol there is similarly obtained propylene glycol acetal of p-bromophenoxypivalophenone, which in Step D, on reaction with n-octadecanal provides propylene glycol acetal of 4'-(α-hydroxy-α-heptadecyl-p-tolyloxy)-pivalophenone.

EXAMPLE 2.

Repeating the procedure of Example 1, but replacing the n-octadecanal used in Step D with an approximately equivalent amount of:
a. propionaldehyde;
b. n-decanal;
c. n-dodecanal;
d. n-tetradecanal; or
e. n-hexadecanal; there is similarly obtained:
a. 4'-(α-hydroxy-α-ethyl-p-tolyloxy)-pivalophenone, ethylene glycol acetal;
b. 4'-(α-hydroxy-α-nonyl-p-tolyloxy)-pivalophenone, ethylene glycol acetal;
c. 4'-(α-hydroxy-α-undecyl-p-tolyloxy)-pivalophenone, ethylene glycol acetal;
d. 4'-(α-hydroxy-α-tridecyl-p-tolyloxy)-pivalophenone, ethylene glycol acetal; and
e. 4'-(α-hydroxy-α-pentadecyl-p-tolyloxy)-pivalophenone, ethylene glycol acetal.

EXAMPLE 3.

Following the procedure of Example 1, but using in place of 4-bromodiphenyl ether used in Step A, thereof, an equivalent amount of:
a. 1-bromo-4-(m-tolyxy)-benzene;
b. 1-bromo-4-(o-fluorophenoxy)-benzene;
c. 1-bromo-4-(m-chlorophenoxy)-benzene;
d. 1-bromo-4-(o-tolyoxy)-3-chlorobenzene;
e. 1-bromo-4-(o-ethylphenoxy)-2-chlorobenzene;
f. 5-bromo-2-phenoxytoluene;
g. 1-bromo-4-(m-chlorophenoxy)-3-chlorobenzene;
h. 1-bromo-4-(o-chlorophenoxy)-benzene; and
i. 1-bromo-4-phenoxy-2-chlorobenzene; there is similarly obtained as final product:
a. 4'-(α-hydroxy-α-heptadecyl-3-methyl-p-tolyloxy)-pivalophenone, ethylene glycol acetal;
b. 4'-(α-hydroxy-α-heptadecyl-2-fluoro-p-tolyloxy)-pivalophenone, ethylene glycol acetal;
c. 4'-(α-hydroxy-α-heptadecyl-3-chloro-p-tolyloxy)-pivalophenone, ethylene glycol acetal;
d. 3'-chloro-4'-(α-hydroxy-α-heptadecyl-2-methyl-p-tolyloxy)-pivalophenone, ethylene glycol acetal;
e. 2'-chloro-4'-(α-hydroxy-α-heptadecyl-2-ethyl-p-tolyloxy)-pivalophenone, ethylene glycol acetal;
f. 3'-methyl-4'-(α-hydroxy-α-heptadecyl-p-tolyloxy)-pivalophenone, ethylene glycol acetal;
g. 3'-chloro-4'-(α-hydroxy-α-heptadecyl-3-chloro-p-tolyloxy)-pivalophenone, ethylene glycol acetal;
h. 4'-(α-hydroxy-α-heptadecyl-2-chloro-p-tolyloxy)-pivalophenone, ethylene glycol acetal; and
i. 2'-chloro-4'-(α-hydroxy-α-heptadecyl-p-tolyloxy)-pivalophenone, ethylene glycol acetal.

What is claimed is:
1. A compound which is an acetal of the formula

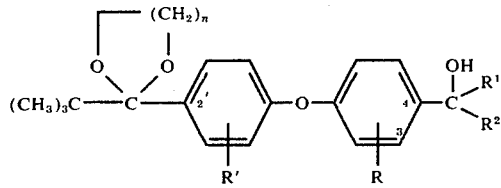

wherein each of
R and R' is, independently, a hydrogen atom, alkyl having from 1 to 4 carbons, or a halogen atom having an atomic weight of from about 19 to 36;
$R^1$ is alkyl having from 1 to 24 carbon atoms;
$R^2$ is a hydrogen atom or alkyl having from 1 to 4 carbon atoms; and
n is 1
provided that when any of R is at the 3-position, or R' is at the 2'-position, such substituent is not branched chain alkyl,
2. A compound of claim 1 in which each of R, R' and $R^2$ is a hydrogen atom.
3. A compound of claim 1 in which $R^1$ is alkyl having from 1 to 4 carbon atoms.
4. A compound of claim 1, in which $R^1$ is alkyl having from 5 to 24 carbon atoms.
5. A compound of claim 1 in which $R^1$ is alkyl having from 10 to 20 carbon atoms.
6. A compound of claim 5 in which each of R, R' and $R^2$ is a hydrogen atom.
7. The compound of claim 6 which is 4'-(α-hydroxy-α-heptadecyl-p-tolyloxy)-pivalophenone, ethylene glycol acetal.
8. A compound of claim 1 which is 4'-(α-hydroxy-α-ethyl-p-tolyloxy)-pivalophenone, ethylene glycol acetal.
9. A compound of claim 1 which is 4'-(α-hydroxy-α-pentadecyl-p-tolyloxy)-pivalophenone, ethylene glycol acetal.
10. A pharmaceutical composition useful in treating diabetes comprising an anti-diabetic effective amount of a compound of claim 1, and a pharmaceutically acceptable carrier.

11. A composition of claim 10 in unit dosage form in which the compound is present in an amount of from about 190 to about 1,500 milligrams.

12. A composition of claim 10 in which the compound is 4'-(α-hydroxy-α-heptadecyl-p-tolyloxy)-pivalophenone, ethylene glycol acetal.

13. A method of treating diabetes in a mammal, comprising administering to a mammal in need of such treatment, an amount of a compound of claim 1, effective in reducing the level of glucose in the blood of said mammal.

14. A method of claim 13 in which the compound is administered in an amount of from about 10 to about 200 milligrams per kilogram of animal body weight daily.

15. A method of claim 13 in which the compound is administered in an amount of from about 750 milligrams to about 3,000 milligrams daily.

16. A method of claim 13 in which the compound is 4'-(α-hydroxy-α-heptadecyl-p-tolyloxy)-pivalophenone, ethylene glycol acetal.

* * * * *